United States Patent
Baier et al.

(10) Patent No.: US 8,534,500 B2
(45) Date of Patent: Sep. 17, 2013

(54) REFILL PACK FOR A PERSONAL USE DEVICE

(75) Inventors: Florian Baier, Frankfurt am Main (DE); Bernhard Boland, Frankfurt am Main (DE); Michael Schmid, Frankfurt am Main (DE); Michael Sauer, Bad Camberg (DE); Michael Stolper, Eschborn (DE)

(73) Assignee: Braun GmbH, Kronberg (DE)

( * ) Notice: Subject to any disclaimer, the term of this patent is extended or adjusted under 35 U.S.C. 154(b) by 404 days.

(21) Appl. No.: 12/600,761

(22) PCT Filed: May 26, 2008

(86) PCT No.: PCT/EP2008/004164
§ 371 (c)(1),
(2), (4) Date: Jul. 8, 2010

(87) PCT Pub. No.: WO2008/145322
PCT Pub. Date: Dec. 4, 2008

(65) Prior Publication Data
US 2010/0294809 A1    Nov. 25, 2010

(30) Foreign Application Priority Data
May 30, 2007    (DE) .......................... 10 2007 025 387

(51) Int. Cl.
*B65D 35/22*    (2006.01)
(52) U.S. Cl.
USPC .............................. 222/94; 222/106; 132/308

(58) Field of Classification Search
USPC ............... 222/92–97, 105, 107, 206–215, 52, 222/56, 61, 63; 132/290, 308, 313, 314
See application file for complete search history.

(56) References Cited

U.S. PATENT DOCUMENTS

| | | | |
|---|---|---|---|
| 3,105,615 A | 10/1963 | Motoyuki Koga | |
| 5,186,559 A | 2/1993 | Fu | |
| 5,207,355 A * | 5/1993 | Thomsen | 222/95 |
| 5,372,487 A * | 12/1994 | Pekar | 417/480 |

(Continued)

FOREIGN PATENT DOCUMENTS

| | | |
|---|---|---|
| DE | 696 10 858 T2 | 3/2001 |
| DE | 199 63 218 A1 | 7/2001 |

(Continued)

OTHER PUBLICATIONS

EP International Search Report for PCT/EP2008/004164 dated Aug. 26, 2008.

(Continued)

*Primary Examiner* — Lien Ngo
(74) *Attorney, Agent, or Firm* — John P. Colbert

(57) ABSTRACT

The present invention relates to a personal use device, preferably a toothbrush, a shaving device, or a hair removal device. The invention relates to a refill pack for such a personal use device, having a supply container (2), particularly a supply bag, containing at least one hygiene or care substance such as toothpaste or the like, and a pump (3) tightly connected to the supply container, the pump chamber of which is connected to the interior (6) of the supply container via an input valve (5). By deformation of a membrane which bounds the pump chamber (7), the pump chamber volume can be changed. The invention also relates to a method for filling such a refill pack.

23 Claims, 5 Drawing Sheets

(56) References Cited

U.S. PATENT DOCUMENTS

Figure 3:
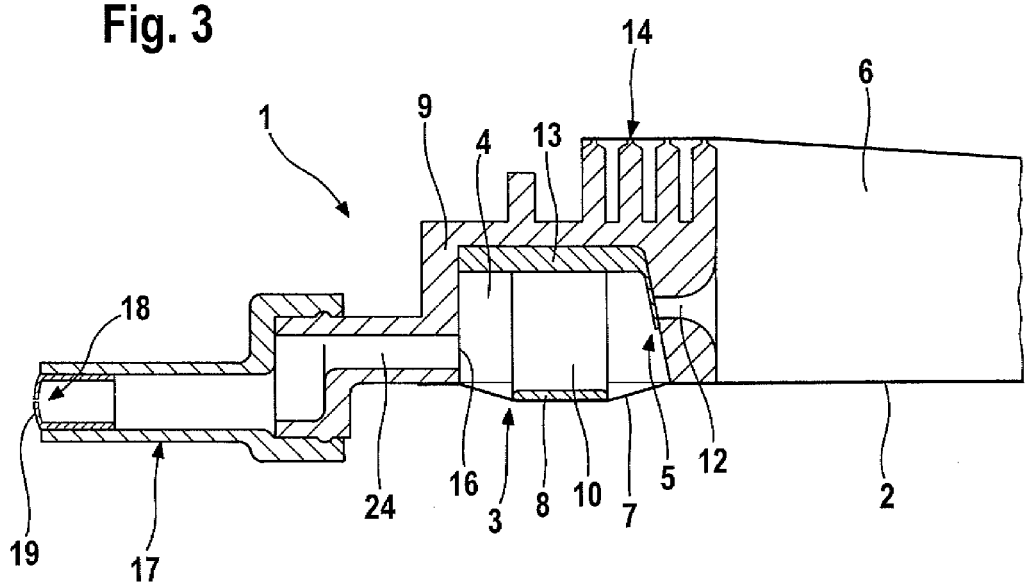

| | | | | |
|---|---|---|---|---|
| 5,388,728 | A | * | 2/1995 | Gueret ............................ 222/105 |
| 5,918,995 | A | * | 7/1999 | Puurunen ........................ 401/146 |
| 5,993,180 | A | * | 11/1999 | Westerhof et al. ............. 417/571 |
| 6,648,641 | B1 | * | 11/2003 | Viltro et al. ...................... 433/80 |
| 6,789,706 | B2 | * | 9/2004 | Abergel et al. ................ 222/207 |
| 7,419,322 | B2 | * | 9/2008 | Laflamme et al. ......... 401/188 R |
| 7,993,067 | B2 | * | 8/2011 | Hall et al. .................. 401/188 R |
| 8,028,708 | B2 | * | 10/2011 | Molema et al. ................. 132/292 |
| 8,118,194 | B2 | * | 2/2012 | Molema et al. ................ 222/207 |
| 2003/0056307 | A1 | | 3/2003 | Tybinkowski et al. |
| 2006/0186140 | A1 | | 8/2006 | Kanfer et al. |
| 2010/0003068 | A1 | * | 1/2010 | Greene et al. .................. 401/282 |

FOREIGN PATENT DOCUMENTS

| | | |
|---|---|---|
| DE | 10 2004 040 834 | 4/2006 |
| EP | 0446513 A1 | 9/1991 |
| EP | 1598118 A1 | 11/2005 |
| EP | 1717159 A2 | 11/2006 |
| EP | 1779933 A1 | 5/2007 |
| GB | 2 184 493 A | 6/1987 |
| GB | 2362354 A | 11/2001 |
| JP | 11 508473 T | 7/1999 |
| WO | WO 93/22200 A1 | 11/1993 |
| WO | WO 02/16047 | 2/2002 |
| WO | WO 03/097250 | 11/2003 |
| WO | WO 2004/082849 | 9/2004 |
| WO | WO 2005/046882 | 5/2005 |

OTHER PUBLICATIONS

DE Search Report for DE 10 2007 025 387.9.

* cited by examiner

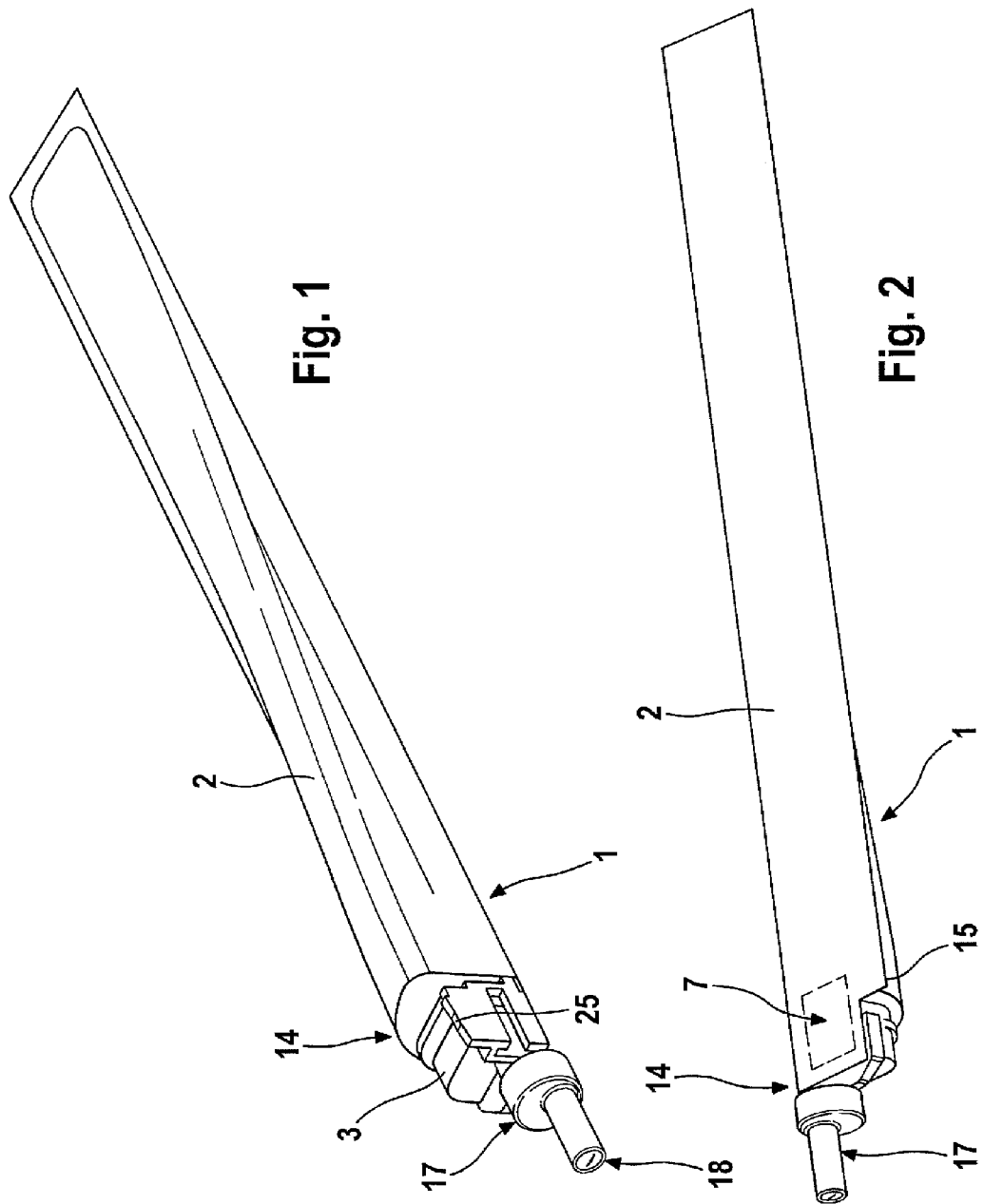

REFILL PACK FOR A PERSONAL USE DEVICE

The present invention relates to a device for personal use, preferably a toothbrush, a shaving device, or a hair removal device. On the one hand, the present invention relates to a refill pack for such a device for personal use having a supply container, in particular a supply bag, containing at least one care and/or treatment substance that is to be dispensed, such as toothpaste or the like, and having a pump connected fixedly to the supply container whose pump chamber is connected via an inlet valve to the interior of the supply container, and whose volume can be changed through deformation of a membrane that limits the pump chamber. The present invention also relates to a method for filling such a refill pack.

It is known in electrical devices for personal use to convey, in addition to the mechanical processing effect, a substance that supports care or cleaning. For example, electric shavers can convey a pre-shave lotion to the shaving head, where the substance is distributed on the skin in order to enable a closer shave with less skin irritation. The refill containers here are made of flexible material in the form of a bag or of hard plastic in the form of a cartridge, wherein it is placed in a corresponding hollow space in the device and discarded after they become empty.

It is additionally known in electric toothbrushes, to use refill packs containing toothpaste that can be filled into small bags that are coupled in the device. After emptying, they are replaced by new supply containers and are discarded. Because the refill packs are disposable parts with a short lifespan, they should be constructed as economically and with as few parts as possible. In most cases, such packs have a plastic part with a coupling point to the device and a foil that is welded onto the plastic part, wherein single-use or multiple valves are provided at the coupling point in order to seal the bag. In many cases, a closure is sufficient that is opened only once, because the drying out of the substance contained in the supply container can be prevented using other means as soon as the refill pack is loaded into the device.

In order to remove a certain amount of substance from the refill pack and to dispense it, a pump is typically used that can be integrated into the refill pack; cf. EP 1 598 118 A1 or WO 02/16047. In order to meet the cost pressure that exists for these disposable units, the pumps are typically designed as membrane pumps in which a malleable membrane limits the pump chamber, so that the pump chamber volume changes by deformation of the membrane and a pump effect can be achieved. A problem in such membrane pumps is the drying out of the pasty substance contained in the supply container. Over time, moisture can be lost through diffusion through the thin pump membrane, so that the substance in the pump dries out, which is a problem in particular with regard to the required long storage life of such refill packs. On the other hand, in order to convey pasty substances in particular, a sufficiently large partial vacuum must be produced by the pump in order to suction the substance out from the supply container, in particular if a slight drying out has already taken place. This happens only in a pump in which the dead volume is relatively small compared to the discharging volume, and in which the inlet and outlet valves attached to the pump chamber have only very slight air leakages. If air is present in the pump as a compressible medium, the required pressure can no longer be built up, which can result in failure of the system.

In order to produce the necessary suction force for the suctioning of pasty substances from the supply container into the pump chamber in sufficient quantity, the membrane is often produced in the form of a dome-shaped bulge made of elastomeric material having thickness sufficient that the membrane, after being pressed into the pump chamber, produces reset forces large enough to cause a corresponding increase in the volume of the pump chamber, and thus a suctioning of the substance into the pump chamber; cf. for example DE 199 63 218 A1 or DE 10 2004 040 834. WO 2004/082849 A1 also describes a refill pack having an integrated membrane pump in which the membrane is to be designed in the form of a dome-shaped curved pushbutton. In this process is proposed that the material of the foil bag can also be used for the membrane, which however creates the condition that as bag material a correspondingly elastic foil material has to be used in order to achieve the desired suction effect.

Such constructions of the pump and its membrane are however often problematic with regard to the drying out of the substance in the pump, to the extent that liquid can exit through the membrane via diffusion over time. On the other hand, the cost pressure to which such disposable packs are subject is difficult to meet.

From this, the present invention is based on the object of creating an improved device for personal use of the type named above, an improved refill pack therefor, as well as a method for the improved filling of such a refill pack, which avoid the disadvantages of the prior art and further develop the prior art in an advantageous manner. Preferably, a design of the refill pack that is very simple and economical to produce will ensure a problem-free functioning of the pump integrated into the refill pack, and will prevent drying out of substances contained in the refill pack.

The invention thus departs from the path followed thus far of achieving the filling of the pump chamber and the suctioning of the substance into this pump chamber through resetting forces of the membrane, and designing the membrane with a correspondingly high degree of elasticity for this purpose. Because the membrane itself no longer has to apply the resetting forces, it is no longer subject to the boundary conditions necessary to achieve the elasticity, so that on the one hand it can be produced more economically and on the other hand it can be designed with fewer difficulties with regard to drying out. According to the invention, it is provided that the membrane is made of a flexible foil and is pressed into a position that enlarges the pump chamber volume by a spring situated in the pump chamber. Here, "flexible" does not necessarily mean the complete absence of any elasticity. However, the foil that forms the membrane is too flexible, or its elasticity is too weak, to overcome the flow resistance of the substance and the blocking of the inlet valve situated upstream of the pump chamber. The reset forces of the membrane are applied by a spring that is situated separately in the pump chamber, so that the construction of the membrane is no longer determined by an elasticity that has to apply the reset forces.

In particular, in a development of the invention, the foil of the membrane forms a barrier that is permanently gas-tight and diffusion-tight. In this way, a drying out of the substance contained in the pump chamber can be prevented, because the exiting of moisture by diffusion through the membrane is prevented, even if the pump is not used for several months, due to the often long storage time of such refill packs. On the other hand, air is also reliably prevented from entering into the pump chamber, which improves the conveying effect given a lack of air, with its compressibility, present in the pump chamber.

In order to achieve the desired barrier effect, the foil can have a multilayer design, and can have at least one barrier layer made of metal, preferably aluminum, which is applied on at least one bearer layer made of plastic, preferably polyethylene, which gives the foil sufficient strength and durability as a whole.

In this process, in particular, the membrane can be made of the same foil as the supply container itself. In an especially preferred development of the invention, a segment of the foil forming the supply container can itself form the membrane of the pump, in particular in such a way that the foil of the supply container is drawn over a pump chamber housing that forms the pump chamber so that the foil of the supply container covers the pump chamber. Alternatively, however, the membrane of the pump can also be designed in the form of a separate foil piece that is fastened on the pump chamber housing, preferably with a material bond, in particular being welded on and/or glued on, and that covers the pump chamber as a membrane. However, the above-named embodiment, in which the foil forming the supply container itself simultaneously forms the membrane, is preferred due to the simple and economical manufacture design of the refill pack.

The spring that loads the membrane of the pump, and the inlet valve connected upstream of the pump chamber, can have various designs. In order to create a pump unit that is particularly easy to install and economical to manufacture, in a development of the invention, the spring and the inlet valve are integrally designed in one piece with one another so that they form a common component that can be placed into the pump chamber housing, which is advantageous with regard to economical manufacture, even despite the flexible construction of the membrane.

In principle, the spring and/or the inlet valve can be integrally formed onto the pump chamber housing. However, the spring and the inlet valve are each advantageously designed separately from the pump chamber housing, in particular in the form of an insert that can be placed into the pump chamber.

In an advantageous development of the invention, in order to prevent damage to the membrane through rubbing of the spring against the membrane, the spring comprises a rounded engagement segment with which the spring presses against the membrane. In a preferred embodiment of the invention, the spring can have a compressible lock washer whose outer jacket surface rests on the membrane. Apart from a slight rubbing effect on the membrane, such a compressible lock washer has a simple design without any noticeable influence on the flow through the pump chamber.

The inlet valve, advantageously combined with the spring to form a common component, can, in a preferred embodiment of the invention, have a spring-mounted blocking plate that, from the inside of the pump chamber, lies against the port of an inlet duct that connects the interior of the supply container to the pump chamber, as long as the said inlet valve does not block this connection. The spring mounting of the blocking plate can in particular be carried out in such a way that the blocking plate can be pivoted or tilted away from the port opening of the inlet duct through corresponding pressure in order to at least partially release the flow cross-section of the port opening.

According to an advantageous embodiment of the invention, the blocking plate is integrally formed onto a spring holder that holds the spring and is supported on a wall that limits the pump chamber on the side of the pump chamber situated opposite the membrane.

In order to achieve an embodiment that can be manufactured economically having only a few components, the pump can have an outlet valve that closes the pump chamber at the pressure side that simultaneously forms the closure or connecting piece of the refill pack, and closes the pack. If necessary, the connecting piece of the refill pack can be additionally sealed by an additional closure, preferably a single-use closure that is removed or opened upon the first use of the refill pack in the corresponding device. However, an additional closure of the connecting piece can advantageously be omitted, and the pressure-side outlet valve of the pump chamber can take over the named double function, namely, given a corresponding membrane movement, to prevent the suctioning back of the fluid at the pressure side while on the other hand achieving a protection against drying out of the connecting piece that forms the pump outlet.

The named pressure-side outlet valve of the pump can be designed in various ways. In a development of the invention, the outlet valve comprises a slotted soft membrane as a valve element that opens and closes when the pump is actuated. In particular, the named outlet valve can be designed as a two-component part that has a hard component and an elastic component. The elastic part forms the above-named slotted soft membrane, which can advantageously be curved and that expands due to the applied pressure and opens the valve.

In order to ensure problem-free activation and secure suctioning of the substance stored in the supply container, despite a simple pump construction and the dead space volume of the pump, according to a further aspect of the present invention it is provided that the refill pack is preconditioned in such a way that the pump chamber is flooded, or filled in an essentially air-free fashion, with a liquid and/or pasty substance even before the first activation of the refill pack. That is, already at the point at which the supply container has taken its maximum initial volume and is completely filled as intended for its use, i.e. before the suctioning of the first volume amount from the storage container into the pump chamber, the pump chamber is already flooded, so that the pump can suction ideally. Through such a pre-flooding of the pump, air in the pump is removed as a compressible medium, thus drastically improving the suction performance, because the pump builds up significantly more pressure with an incompressible medium than it does with gas. At the same time, the above-described advantageous design of the pressure-side outlet valve, which at the same time forms the closure or connecting piece of the refill pack, is easily achieved. Whereas in an initial air-operated pump in which the pump chamber is not pre-flooded, the partial vacuum resulting from actuation of the membrane would be calculated, in accordance with the ideal gas law, from the ratio of the compressed air volume relative to the dead volume, and, given a large dead volume, a correspondingly insufficient partial vacuum would result that would additionally decrease due to leakages at the valve, in an already pre-flooded pump the dead volume does not play any larger role. In this way, the pressure-side outlet valve of the pump can also be situated at some distance from the pump chamber itself, and can in particular be provided at the end of a duct that forms one of the connecting collars, and can thus simultaneously be used as a termination of the flow duct, so that a second valve at the pressure side is no longer required.

In principle, the pump can be pre-flooded with the care or treatment substance that is to be dispensed. In a development of the invention, however, it is also possible to pre-flood the pump with some other medium, in particular a maintenance medium that promotes the upkeep of the pump, and which can contain lubricants and/or substances that prevent drying out and seizing. Such a special pre-flooding substance can be optimally aligned, with regard to its viscosity and drying characteristics, to the bearing and to the pump including the valves. In this process, essentially only the pump, and not the supply container connected thereto, is advantageously filled with this other substance, so that upon activation of the device, or the first actuation of the pump of the refill pack, this separate substance is immediately emptied, and immediately hereafter, the care or treatment substance that is to be emitted is dispensed. The substance with which the pump is pre-flooded protects the remaining care or treatment substance from drying out, and helps the pump enter operate.

The flooding of the pump, given the device-side configuration of the refill pack, can in principle take place in a wide variety of ways. According to an advantageous embodiment of the invention, the bag can first be shaped and sealed at its sides oriented away from the pump. The bag is then filled with the care or treatment substance while the pump has not yet been connected to it until an air cushion remains only at the upper open edge of the bag. In the next step, the bag is welded or glued to the pump housing. The excess air still situated in the supply container in the vicinity of the pump or in the pump is pressed out of the bag or is suctioned out by partial vacuum, so that the pump is at least partially flooded with the substance.

Alternatively, even before the filling of the refill container, the pump can be integrated into said container, wherein; in this case, the supply container has another opening at another location, in particular on the side opposite the pump. The filling of the supply container takes place through this segment, which at first still remains open. After the filling, the supply container can be sealed and the excess area can be removed by cutting.

If, above-mentioned process, the pump is to be flooded with a specific other substance, this substance is first brought into the pump and the supply container is then filled with the care or treatment substance that is to be dispensed.

Of course, the refill pack can, in principle, have various shapes and mounting dimensions adapted to the particular device. For use in a toothbrush in particular, but also for other applications, in a development of the invention the refill pack can have a shape that is altogether oblong, or, roughly stated, "sausage-shaped", wherein the pump can be arranged advantageously on the front side of an end segment of the refill pack, and in particular may be welded and/or glued into an edge seam of the supply container. In this process, in an advantageous development of the invention, the connecting piece formed by the pressure outlet of the pump chamber can protrude from the supply container on the front side, or can protrude past this supply container. The orientation of the preferably collar-shaped connecting piece can, in principle, vary and can be adapted to the particular construction of the refill pack connectors on the device. An advantageous realization can consist in that the collar-shaped connecting piece extends essentially parallel to the longitudinal axis of the supply container.

In order to achieve optimal cleaning or care effects, in particular in the area of oral care, it can make sense to convey two or more substances one after the other, or parallel to each other. For this purpose, in a development of the invention, the refill pack may be altogether divided into at least two subunits for dispensing at least two substances that are different or of the same type. The refill pack then forms, so to speak, a double pack for conveying and dispensing two substances.

Here, in a development of the invention, the refill pack can have a supply container having two separate storage chambers, or, alternatively, also a plurality of separate supply containers, wherein each of the plurality of storage chambers or of supply containers advantageously has a respective inlet valve that can communicate with separate pump chambers, so that each substance can be dosed individually.

If the substances are to be dispensed in parallel from the subunits of the refill pack, the pump chambers can convey using common output duct.

In order to enable separate dispensing with regard to time or space, in a development of the invention, it is however advantageously provided that the plurality of subunits of the refill pack each have separate, preferably collar-shaped connecting pieces, by which the corresponding substances can be separately dispensed. Here, in a development of the invention, the connecting pieces communicate with the above-named separate pump chambers by which the corresponding substances can be drawn separately from the storage chambers or from the plurality of supply containers.

In order to enable the corresponding multiple pack, despite its plurality of subunits, to be handled in the same manner as a simple pack, in a development of the invention, it is provided that the plurality of connecting pieces of the subunits are held in a predetermined position and/or in a predetermined orientation relative to one another.

In order to enable simple connection, but also with regard to a compact design, it is advantageous if the plurality of connecting pieces of the multiple pack are situated at small distances from one another. Connecting pieces arranged very close to one another can be more easily brought into contact with connecting pieces on the device, which then are also arranged close to one another, than can the connecting pieces which are arranged far away from one another or arranged on different sides of the refill pack. In a development of the invention, the connecting pieces are arranged with a distance of less than 20 mm from one another, preferably even less than 15 mm. A particularly simple connection can be achieved if the distance of the connecting pieces is less than 10 mm from one another, because in this way the connecting pieces can easily be placed uniformly onto the corresponding device-side connecting pieces with a linear movement, without a slight oblique guiding causing a larger tilting of one of the connecting pieces.

The multiple connecting pieces of the multiple pack can, for this purpose, in principle be held in position in various ways. According to an advantageous embodiment of the invention, the positioning can take place via the design of the pump itself. In particular, the pump can be constructed in the form of a double pump or multiple pump in which the multiple pump chambers and the connecting pieces going out there from are designed in a common, preferably one-piece, pump chamber housing.

Alternatively, separate pump units, and in particular separate pump chamber housings, may also be provided, wherein, in this case, the multiple connecting pieces of the multiple pack are held next to one another by a positioning piece that is placed onto the multiple pump units and/or the connecting pieces thereof. Through such a positioning piece, the subunits can be operated in the manner of a simple pack even given completely separate construction of the subunits.

The preferably collar-shaped connecting pieces onto which the pressure-side outlet valve of the respective pump chamber is advantageously formed can be designed separately from the pump chamber housing and, in a development of the invention, can be placed onto this housing with a positive fit. In order to further reduce the number of parts, in a development of the invention, the connecting pieces can also be advantageously integrally formed onto the pump housing. In this way, the refill pack can be manufactured with a minimum number of components.

In particular, the refill pack can be made up of five or fewer parts, preferably four or fewer parts, and in particular can be made up of only three parts, namely the pump housing with the connecting piece or pressure-side outlet valve integrally formed thereon, the spring that pre-tensions the membrane in the pump housing with the outlet valve integrally formed thereon, and, finally, the supply container itself, which can be materially bonded to the pump housing, in particular welded thereto. If, above-mentioned process, the connecting piece with the pressure-side outlet valve integrally formed thereon is designed separately, four parts are correspondingly provided. Given the design of the refill pack in the form of a multiple pack having a plurality of subunits, the named number of parts holds for each applies, wherein in this case however, the named number of parts may also apply for the complete multiple pack if the pump, or its pump housing, is designed in the form of a multiple pump, wherein spring units that are separate for each pump chamber may optionally result in a corresponding increase in the number of parts.

These and further features, independent of their characterization in the claims in combination and subcombination with one another may form the subject matter of the present invention even, result not only from the claims but also from the drawings and from the following description of preferred exemplary embodiments.

Figure 4:
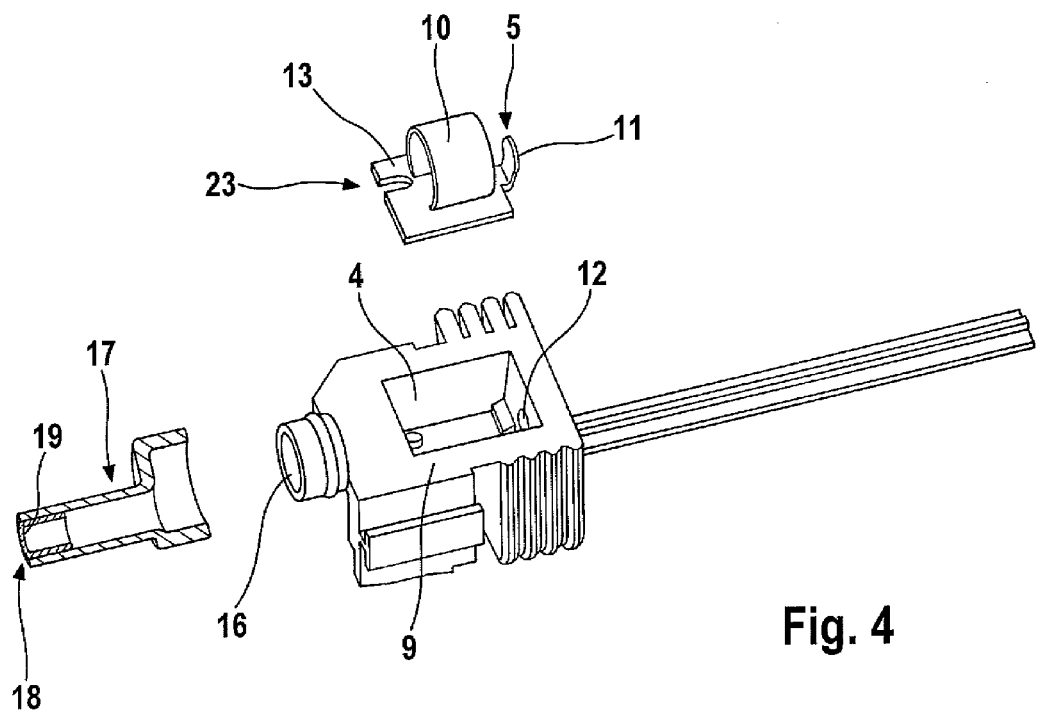
Figure 5:
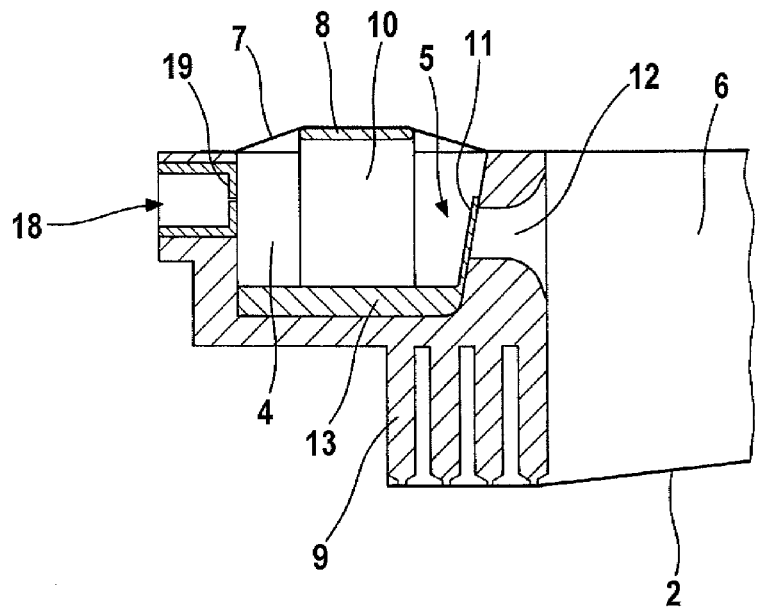
Figure 6:
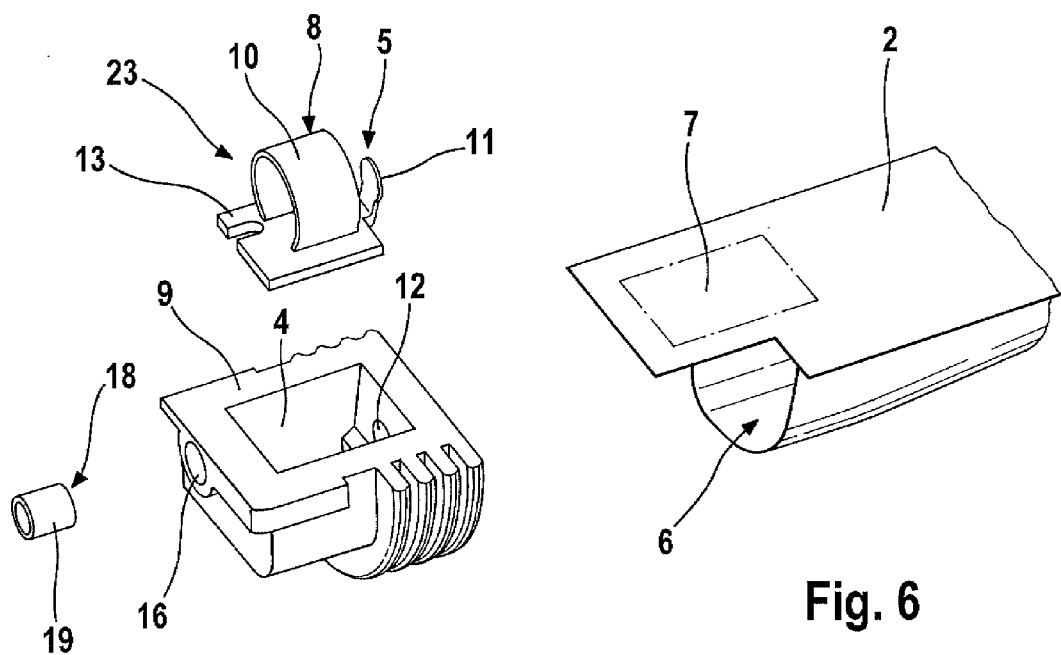
Figure 7:
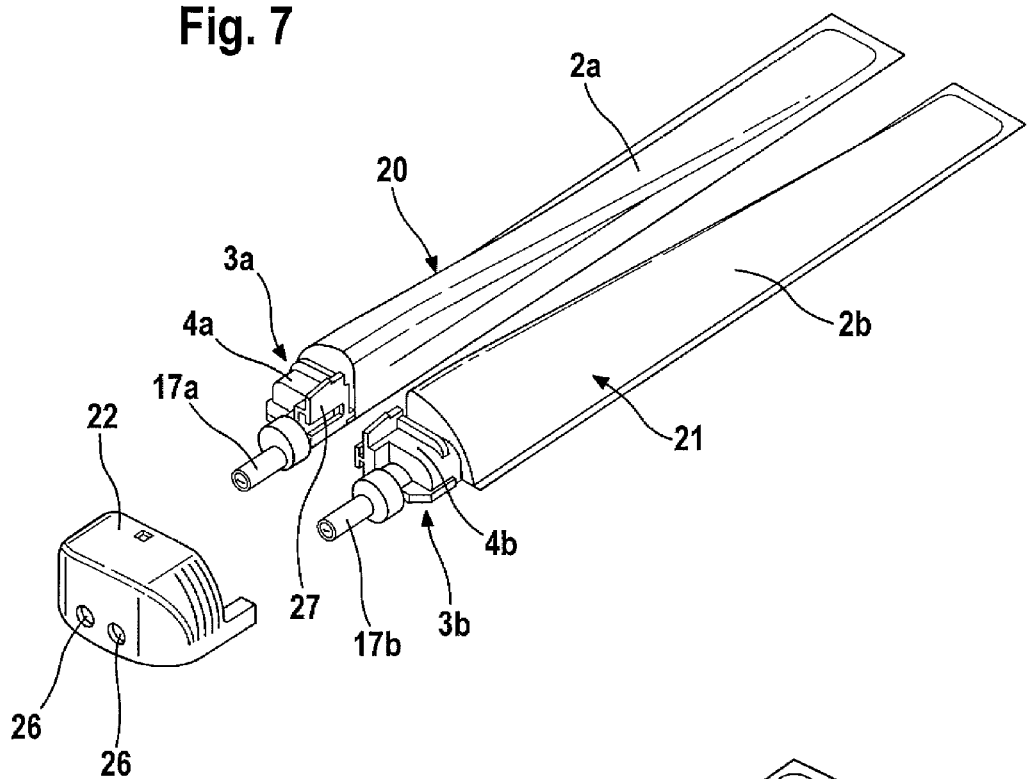
Figure 8:
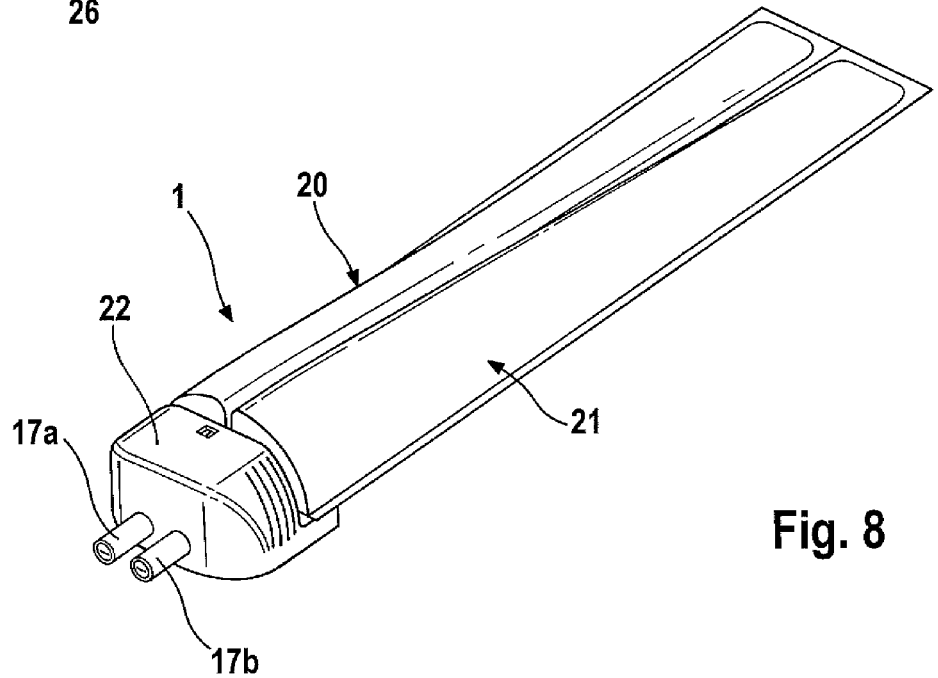
Figure 9:
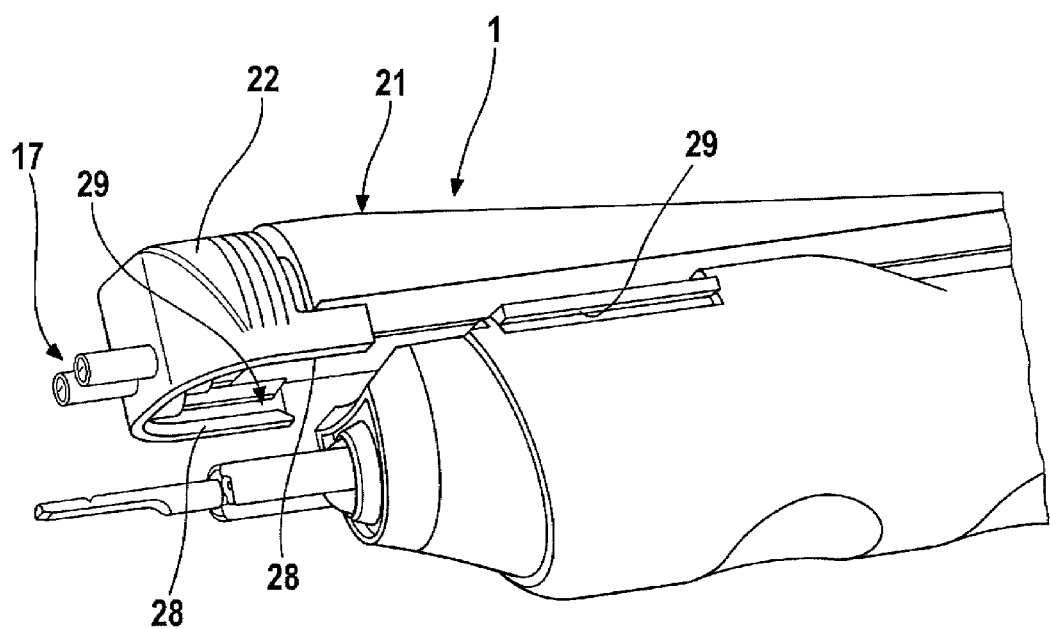

FIG. 1 shows a perspective side view of a refill pack for a toothbrush according to a first advantageous embodiment of the invention, which shows the pump provided at one end face on the supply container, FIG. 2 shows a schematic perspective side view of the refill pack from FIG. 1, which shows the membrane of the pump, FIG. 3 shows a longitudinal cross-section of a through the refill pack of the preceding Figures, which shows the design of the pump and its connection to the supply container, FIG. 4 shows a perspective exploded view of the pump of the refill pack from the preceding Figures, FIG. 5 shows a longitudinal cross-section similar to FIG. 3 through the pump of the refill pack according to an alternative embodiment, FIG. 6 shows a perspective exploded view of the embodiment from FIG. 5, FIG. 7 shows a schematic perspective view of a refill pack in the form of a double pack having two separate subunits according to a further advantageous embodiment of the invention, wherein the two subunits and a positioning piece that holds them together are shown in an exploded view, FIG. 8 shows a schematic perspective view of the double refill pack from FIG. 7 in the ready-to-use assembled state, and FIG. 9 shows a perspective functional view that shows the placement of the double refill pack of FIGS. 7 and 8 onto the handle of a toothbrush.

The refill pack 1, shown in FIGS. 1 through 4, holds toothpaste and can be placed into an electric toothbrush that conveys the toothpaste contained therein out of said refill pack 1. The refill pack 1 has a contour that is altogether oblong, and can roughly be said to be "sausage-shaped", wherein the cross-section of the refill pack 1 tapers towards one of its ends; cf. the right end in FIG. 1. The refill pack 1 comprises an oblong supply container 2, having the named sausage-shaped contour with a flattened end that, in the depicted embodiment, is designed as a foil bag that is welded together from a flat foil or from flat foil pieces. Here, the supply container 2 can in particular be made of a permanently gas-tight and diffusion-tight barrier foil that can have a multilayer construction, and in particular can have a barrier layer made of aluminum and at least one bearer layer made of polyethylene.

On the front side of the supply container 2 arranged opposite the flattened end of the supply container 2, a pump 3 is integrated into this container, said pump having a pump chamber housing 9 that is partially integrated in the interior 6 of the supply container 2; cf. FIG. 3. The named housing 9 of pump 3 is welded into edge area 14 of the front side of the supply container 2, in the edge seam 15 thereof, so that the pump 3 is connected in gas-tight fashion to the supply container 2.

As is shown in particular in FIGS. 3 and 4, a pump chamber 4 is designed in the pump chamber housing 9 that, in view of the pump chamber housing 9, is open toward one side only. This open side of the pump chamber 4 is closed by a membrane 7 that completely covers the open side of the pump chamber 4, which is clearly visible in FIG. 4, and is materially bonded to the pump chamber housing 9 in a gas-tight fashion along the edge of the pump chamber opening, in particular by welding and/or adhesive.

As is shown in FIGS. 2 and 3, the membrane 7 of the pump 3 is formed by the wall of the supply container 2, which is designed as a foil bag; i.e., the foil of the supply container 2 is drawn over the pump chamber housing 9 far enough that the foil of the supply container 2 forms the membrane 7.

Because the foil of the supply container 2 is flexible, i.e. does not itself have the elasticity necessary to reset the membrane 7 into the position in which it enlarges the volume of the pump chamber 4, and thus the toothpaste is suctioned from the supply container 2 into the pump chamber 4, in the pump chamber 4 a spring 8 is provided that presses against the membrane 7 from the inside of the pump chamber 4, and presses this membrane into the position in which it increases the volume of the pump chamber. However, the membrane 7 is elastic enough that it can be pressed a certain distance into the pump chamber 4 against the pre-tension force of the spring 8. In order to enlarge the stroke volume, the membrane 7 can also be placed over the pump chamber 4 so loosely and with enough slack, so to speak, that a corresponding pump movement can be carried out, even with the small or no stretchability of the membrane 7.

As FIG. 3 shows, the pump chamber 4 is connected to the interior 6 of the supply container 2 in the pump chamber housing 9 via an inlet duct 12 designed in said housing, wherein this connection is made through an inlet valve 5 in such a way that the inlet duct 12 opens when there is an increase in the volume of the pump chamber 4 and is closed when there is a decrease in the volume of the pump chamber 4.

As FIG. 4 shows, the inlet valve 5 and the spring 8 are advantageously combined to form a common component designed in one piece. In the depicted embodiment, the spring 8 comprises a lock washer 10 that is mounted on a plate-shaped spring holder 13 on which the inlet valve 5 is also integrally formed at one end. The component comprising the spring 8 and the inlet valve 5 forms an insert 23 that fits precisely into the pump chamber 4.

In the depicted embodiment, the inlet valve 5 is designed in the form of a blocking plate 11 that is placed from the inside onto the port of the inlet duct 12 that connects the pump chamber 4 to the interior 6 of the supply container 2. Here, the blocking plate 11 can execute spring-loaded movements relative to the spring holder 13, in particular by pivoting, so that it can release the port of the inlet duct 12 when a partial vacuum arises in the pump chamber 4.

At the pressure or outlet side, the pump chamber 4 is connected to a connecting piece 17 that protrudes from the front side of the supply container 2, in which the connecting piece is designed with an outlet duct 24 having a circular cross-section. In the depicted embodiment according to FIGS. 3 and 4, the named outlet duct 24 comprises two segments that are offset to one another in the transverse direction; cf. FIG. 3. On a first segment of the outlet duct 24 that is integrally formed onto the pump chamber housing 9, a separate connecting piece 17 is placed with a positive fit, so as to be fluid-tight and preferably also gas-tight, in which a second segment of the outlet duct 24 is designed. At one front side of the connecting piece 17, an outlet valve 18 is provided that on the one hand forms the pressure-side valve of the pump 3 and on the other hand simultaneously forms a closure that seals in air-tight fashion of the supply container 2 or the interior of the pump 3, and in this way protects the substance contained therein from drying out.

In the depicted specific embodiment, the outlet valve 18 is designed in the form of a two-component part. In the body of the connecting piece 17, which is injected from hard plastic, a slotted soft membrane 19 is provided that closes the connecting duct 24 on the front side and in the depicted embodiment is spherically curved; cf. FIG. 3. The outlet valve 18 can open and close through elastic deformation of the soft membrane 19.

In order to reduce the number of components still further, the above-described connecting piece 17 can also be integrally formed in one piece onto the pump chamber housing 9. FIG. 5 shows such an embodiment. The outlet valve 18 that closes the pressure side of the pump 3 can be built into the outlet duct 24, which extends in the pump chamber housing 9. For this purpose, the pump chamber housing 9 can advantageously be injection-molded in a two-component technique, so that the outlet valve 19 is injected into the body, made of hard plastic, of the pump chamber housing 9, in the form of the soft membrane 19 shown in FIG. 5. Similar to the above-described embodiment, in FIG. 5 the membrane 7 is also formed by the wall of the supply container 2. FIG. 6 shows this in an exploded view in which the foil segment of the supply container 2, which extends over the pump chamber 4, is clearly visible.

There are various ways to fill the supply container 2 in the above-described manner in such a way that the pump 3 is also flooded with pasty or liquid substance. According to an embodiment of the invention, in a first step, the supply container 2 is formed as a bag and is sealed on the lower side. The bag is then filled with the care substance until an air cushion remains at the top. In the next step, the bag forming the supply container 2 is welded to the pump chamber housing 9 and is sealed in this way. The excess air is pressed out of the bag or is suctioned out by partial vacuum, so that the pump 3 is also at least partly, and preferably completely, flooded with substance.

Alternatively, before the filling, the housing 9 of the pump 3 can also be welded to the segments of the foil of the supply container 2 provided for this purpose, so that a supply container is formed that is open at its lower side, i.e. the side situated opposite the pump 3. The filling of the container takes place from the lower side through the opening that remains open. After filling, the foil is sealed and the excess area can be removed by cutting.

During the filling it can also be provided that a substance that is different from the care or cleaning substance that is to be dispensed from supply container 2 can be brought into the interior of the pump 3, in particular into the pump chamber 4. During the filling, this other substance is provided in such a way that essentially only the pump 3 is filled with this substance. During use of the device, this substance is the first to be conveyed, and immediately after this, the care or cleaning substance with the optimal care properties is dispensed. This pump filling protects the remaining substance from drying out and helps the pump enter into operation.

Advantageously, the pump 3 can also have connecting means, preferably connecting contours 25 that bring about a positive connection, which facilitate a precise positioning of the refill pack 1 in a corresponding device. As FIG. 1 shows, these connecting contours 25 can be designed in the form of positively connecting projections and/or recesses that can be precisely fit on corresponding contour segments on the device.

FIGS. 7 through 9 show another advantageous embodiment of the invention, according to which the refill pack 1 can also be designed in the form of a multiple pack, wherein, in FIGS. 7 through 9, an embodiment as a double pack is shown. However, if needed, a division into more than two subunits 20 and 21 can take place.

In the embodiment shown in FIGS. 7 through 9, the two subunits 20 and 21 are designed completely separate from one another. Here, each subunit 20 and 21 essentially corresponds to an individual refill pack, as was shown in FIGS. 1 through 6.

As FIGS. 7 and 8 illustrate, a positioning piece 22 is advantageously provided here that holds the two subunits 20 and 21 in a defined position to one another, and in particular fixes the two connecting pieces 17 of the two subunits 20 and 21 in a precisely defined position to one another, so that the double pack can be handled in the manner of a single pack, and in particular can be precisely placed into or onto corresponding connecting pieces on the device.

As FIG. 7 shows, the positioning piece 22 can be designed in particular in the form of a plug-on cap that has receptacle recesses 26 in which the connecting pieces 17 are integrated. In the depicted form, these recesses 26 are designed in the form of through-holes through which the connecting pieces 17 can be inserted.

As FIG. 7 shows, the contours of the two subunits 20 and 21 are aligned on each another so that they are placed tightly against one another when they are connected by the positioning piece 22. Here, the contour alignment can be provided in particular in the form of flat sides 27 or flattened areas that can extend over the supply container 2 and/or over the pump chamber housing 9.

The positioning piece 22 advantageously comprises an inner contour that is aligned to the front side outer contour of the refill pack 1 and its subunits 20 and 21, in order to bring about a positive connection between the positioning piece 22 and the refill pack 1 beyond the connecting pieces 17 thereof. In this way, the subunits 20 and 21 are fitted precisely and tightly on the positioning piece 22.

As FIG. 9 illustrates, on the refill pack 1, in particular the positioning piece 22 thereof, the positioning means 28 are further provided for positioning with a precise fit on a part of the device, in particular a handle of the toothbrush, wherein said means holds the refill pack 1 on the device part in a predetermined position. Advantageously, the positioning means 28 can be designed in the form of positively connecting fastening means that hold the refill pack 1 on the device part with a positive fit. In the depicted embodiment, the positioning means 28 comprise a sliding guide that comprises one or more projections and one or more slot-type recesses that can be pushed into one another and that hold the refill pack 1 on the device part in the pushed-together position. As FIG. 9 illustrates, the refill pack 1 extends along the device handle on its circumference, wherein the connecting pieces 17 of the refill pack 1 projecting at the front side of the device handle and extending approximately parallel to the insertion shaft of the toothbrush handle, so that the brush attachment can be brought into engagement simultaneously with the drive shaft and with the connecting pieces 17 of the refill pack 1 through a simple sliding movement.

The distance of the two connecting pieces 17 from one another is advantageously less than 20 mm, preferably less than 15 mm, and in particular approximately 10 mm.

What is claimed is:

1. A refill pack for an electric toothbrush, having a supply container that contains at least one oral care substance that is to be dispensed, as well as a pump that is fixedly connected to the supply container; whose pump chamber is connected via an inlet valve to the interior of the supply container and whose volume can be changed through deformation of a membrane that limits the pump chamber, wherein the supply container and the membrane consists of a flexible foil and wherein the membrane is pressed into a position that enlarges the volume of the pump chamber by a spring situated in the pump chamber; and wherein the pump is integrated into the supply container, and the membrane of the pump is formed by a segment of the foil that forms the supply container.

2. The refill pack according to claim 1, wherein the foil of the membrane forms a permanently gas-tight and/or diffusion-tight barrier.

3. The refill pack according to claim 1, wherein the foil of the membrane has a multilayer construction and has at least one barrier layer made of metal on at least one bearer layer made of plastic.

4. The refill pack according to claim 1, wherein the membrane is made of the same foil as the supply container.

5. The refill pack according to claim 1, wherein the spring and the inlet valve of the pump chamber form a component that is designed integrally in one part.

6. The refill pack according to claim 1, wherein the spring and/or the inlet valve are designed separately from a pump chamber housing and form an insert that can be placed into the pump chamber.

7. The refill pack according to claim 1, wherein the spring has a compressible lock washer whose outer jacket surface lies on the membrane of the pump.

8. The refill pack according to claim 1, wherein the inlet valve has a spring-mounted blocking plate that can be placed, from the inside of the pump chamber onto the port of an inlet duct that connects the interior of the supply container to the pump chamber.

9. The refill pack according to claim 8, wherein the blocking plate is formed onto a spring holder that holds the spring.

10. The refill pack according to claim 1, wherein the pump is welded and/or glued into a front sided edge segment of the supply container.

11. The refill pack according to claim 1, wherein a pressure outlet of the pump chamber has at least one collar-shaped connecting piece for connecting the refill pack to a refill pack connection, in order to dispense the oral care substance.

12. The refill pack according claim 11, wherein the connecting piece protrudes from the supply container at an front side and/or extends essentially parallel to a longitudinal axis of the supply container.

13. The refill pack according to claim 11, wherein the pump has an outlet valve that closes the pump chamber at the pressure side, and that simultaneously forms the closure and/or the connecting piece of the refill pack.

14. The refill pack according to claim 13, wherein the outlet valve has a slotted soft membrane as a valve element.

15. The refill pack according to claim 1, wherein the refill pack is divided into at least two subunits for dispensing at least two oral care substances that are different or the same.

16. The refill pack according claim 1, wherein the supply container has two separate supply chambers, and/or two separate storage containers are provided that can be brought into connection with separate pump chambers via a respective inlet valve.

17. The refill pack according to claim 16, wherein the two pump chambers are each capable of being brought into connection at the pressure side with separate, collar-shaped connecting pieces, that are held in a predetermined position relative to one another.

18. The refill pack according to claim 17, wherein the two connecting pieces have a distance from one another of less than 20 mm.

19. The refill pack according to claim 16, wherein the two pump chambers are designed in a common, one-piece, pump chamber housing.

20. The refill pack according to claim 16, wherein two separate pump chamber housings are provided, and the two connecting pieces are held in a predetermined position relative to one another by a positioning piece placed on the two pumps and/or on the connecting pieces.

21. The refill pack according claim 1, wherein the refill pack is made up of five or fewer parts.

22. The refill pack according to claim 21, wherein the refill pack is made up of three parts, namely the pump housing with integrally formed outlet valve, the spring in the pump chamber with integrally formed inlet valve, and the supply container.

23. The refill pack according to claim 15, wherein each subunit is made up of five or fewer parts.

* * * * *